United States Patent
Rao et al.

(10) Patent No.: US 6,734,015 B1
(45) Date of Patent: *May 11, 2004

(54) ISOLATION OF LINEAGE-RESTRICTED NEURONAL PRECURSORS

(75) Inventors: Mahendra S. Rao, Salt Lake City, UT (US); Margot Mayer-Proschel, Sandy, UT (US)

(73) Assignee: University of Utah Research Foundation, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 302 days.

This patent is subject to a terminal disclaimer.

(21) Appl. No.: 08/909,435

(22) Filed: Jul. 4, 1997

(51) Int. Cl.[7] .............................. C12N 5/00; C12N 5/06; C12N 5/08
(52) U.S. Cl. ...................................... 435/368; 435/325
(58) Field of Search ................................. 435/350, 351, 435/352, 325, 368, 363, 353, 354, 366, 377, 378, 383, 384, 387

(56) References Cited

U.S. PATENT DOCUMENTS

| | | | |
|---|---|---|---|
| 5,087,570 A | 2/1992 | Weissman et al. | 435/240.1 |
| 5,411,883 A | 5/1995 | Boss et al. | 435/240 |
| 5,589,376 A | 12/1996 | Anderson et al. | 435/240.2 |
| 5,753,505 A | 5/1998 | Luskin | 435/375 |
| 6,020,197 A | * 2/2000 | Gage et al. | 435/638 |
| 6,040,180 A | * 3/2000 | Johe | 435/377 |

FOREIGN PATENT DOCUMENTS

WO          9301275          * 1/1993

OTHER PUBLICATIONS

Blass–Kampmann et al., J. Neuroscience Research, 37:359–373, 1994.*
Mayer–Proschel et al., Neuron, 19:773–785, 1997.*
Gage, F.H., et al, *Isolation, Characterization and Use of Stem Cells from the CNS*, 18 Ann. Rev. Neurosci. 159–92 (1995).
Marvin, M., et al, *Multipotential Stem Cells in the Vertebrate CNS*, 3 Semin. Cell. Biol. 401–11 (1992).
Davis, A.A., et al, *A Self–Renewing Multipotential Stem Cell in Embryonic Rat Cerebral Cortex*, 362 Nature 363–72 (1992).
Gritti, A.G., et al, *Multipotential Stem Cells from the Adult Mouse Brain Proliferate and Self–Renew in Response to Basic Fibroblast Growth Factor*, 16 J. Neurosci. 1091–1100 (1996).
Reynolds, B.A., et al, *A Multipotential EGF–Responsive Striatal Embryonic Progenitor Cell Produces Nuerons and Astrocytes*, 12 J. Neurosci. 4565–74 (1992).
Reynolds, B.A., et al, *Clonal and Population Analyses Demonstrate that an EGF–Responsive Mammalian Embryonic CNS Precursor is a Stem Cell*, 175 Development Biol. 1–13 (1996).
Williams, B.P., et al, *The Generation of Neurons and Oligodendrocytes from a Common Precursor Cell*, 7 Neuron 685–93 (1991).
Kilpatrick, T.J., et al, *Cloned Multipotential Precursors from the Mouse Cerebrum Require FGF–2, Whereas Gilal Restricted Precursors are Stimulated with Either FGF–2 or EGF*, 15 J. Neurosci. 3653–61 (1995).
Price, J., et al, *Lineage Analysis in the Vertebrate Nervous System by Retrovirus–Mediated Gene Transfer*, 84 Developmental Biol. 156–160 (1987).
Williams, B., et al, *Precursor Cell Types in the Germinal Zone of the Cerebral Cortex*, 17 BioEssays 391–93 (1995).
Anderson, D.J., *The Neural Crest Lineage Problem: Neuropoiesis?*, 3 Neuron 1–12 (1989).
Ray, J., et al, *Spinal Cord Neuroblasts Proliferate in Response to Basic Fibroplast Growth Factor*, 14 J. Neurosci. 3548–64 (1994).
Sommer, L., et al, *The Cellular Function of MASH1 in Automatic Neurogenesis*, 15 Neuron 1245–58 (1995).
Bignami, A., et al, *Localization of the Gilal Fibrillary Acidic in Astrocytes by Immunofluorescence*, 43 Brain Res. 429–35 (1972).

(List continued on next page.)

Primary Examiner—Gary Kunz
Assistant Examiner—Robert C. Hayes
(74) Attorney, Agent, or Firm—Licata & Tyrrell P.C.

(57) ABSTRACT

A self-renewing restricted stem cell population has been identified in developing (embryonic day 13.5) spinal cords that can differentiate into multiple neuronal phenotypes, but cannot differentiate into glial phenotypes. This neuronal-restricted precursor (NRP) expresses highly polysialated or embryonic neural cell adhesion molecule (E-NCAM) and is morphologically distinct from neuroepithelial stem cells (NEP cells) and spinal glial progenitors derived from embryonic day 10.5 spinal cord. NRP cells self renew over multiple passages in the presence of fibroblast growth factor (FGF) and neurotrophin 3 (NT-3) and express a characteristic subset of neuronal epitopes. When cultured in the presence of RA and the absence of FGF, NRP cells differentiate into GABAergic, glutaminergic, and cholinergic immunoreactive neurons. NRP cells can also be generated from multipotent NEP cells cultured from embryonic day 10.5 neural tubes. Clonal analysis shows that E-NCAM immunoreactive NRP cells arise from an NEP progenitor cell that generates other restricted CNS precursors. The NEP-derived E-NCAM immunoreactive cells undergo self renewal in defined medium and differentiate into multiple neuronal phenotypes in mass and clonal culture. Thus, a direct lineal relationship exists between multipotential NEP cells and more restricted neuronal precursor cells present in vivo at embryonic day 13.5 in the spinal cord.

1 Claim, 1 Drawing Sheet

OTHER PUBLICATIONS

Figure 1:
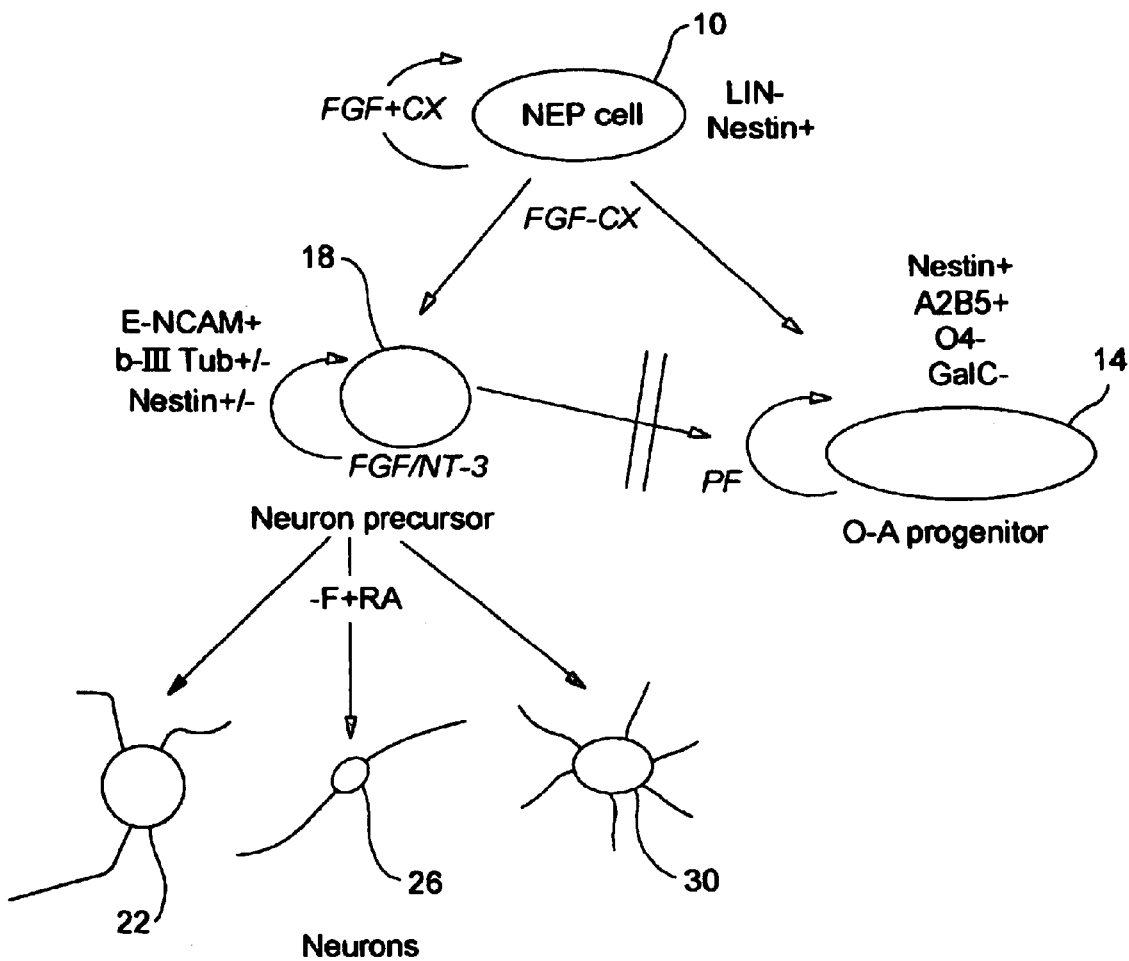

Geisert, E., et al, *The Neuronal Response to Injury as Visualized by Immunostaining of Class β–tubulin in the Rat*, 102 Neurosci. Lett. 137–41 (1989).

Lendhal, U., et al, *CNS Stem Cells Express a New Class of Intermediate Filament Protein*, 60 Cell 585–95 (1990).

Mayer, M., et al, *Ciliary Neurotrophic Factor and Lukemia Inhibitory Factor Promote the Generation, Maturation, and Survival of Oligodendrocytes*, 120 Development 142–53 (1994).

Wysocki, L., et al, *"Panning" for Lymphocytes: A Method for Cell Selection*, 75 Proc. Nat'l Acad. Sci. USA 2844–48 (1978).

Bottenstein, J., et al, *Growth of a Rat Neuroblastoma Cell Line in Serum–free Supplemented Medium*, 76 Proc. Nat'l Acad. Sci. USA 514–17 (1979).

Cattaneo, Elana and McKay, Ron, *Proliferation and Differentation of Neuronal Stem Cells Regulated by Nerve Growth Factor*, Nature, vol. 347, 762–765 (1990).

Bignami, A. et al., *Localization of the Gilal Fibrillary Acidic Protein in Astrocytes by Immunofluorescence*, Brain Research, 43, 429–435 (1972).

Wysocki, L.J. and Sato, V.L., *"Panning" for Lymphocytes: A Method for Cell Selection*, Proc. Natl. Acad. Sci. USA, vol. 75, No. 6, 2844–2848 (Jun. 1978).

\* cited by examiner

ISOLATION OF LINEAGE-RESTRICTED NEURONAL PRECURSORS

STATEMENT REGARDING FEDERALLY SPONSORED RESEARCH OR DEVELOPMENT

This invention was made with government support under a FIRST award from the National Institutes of Health. The government has certain rights in the invention.

BACKGROUND OF THE INVENTION

This invention relates to lineage-restricted intermediate precursor cells and methods of making thereof More particularly, the invention relates to neuronal-restricted precursors (NRP's) isolated from mammalian embryos or mammalian neuroepithelial stem cells. These neuronal-restricted precursors are capable of self-renewal and differentiation into neurons, but not into glia, i.e. astrocytes and oligodendrocytes. Methods of generating, isolating, and culturing such neuronal-restricted precursor cells are also described.

Multipotent cells with the characteristics of stem cells have been identified in several regions of the central nervous system and at several developmental stages. F. H. Gage et al., Isolation, Characterization and Use of Stem Cells from the CNS, 18 Ann. Rev. Neurosci. 159–92 (1995); M. Marvin & R. McKay, Multipotential Stem Cells in the Vertebrate CNS, 3 Semin. Cell. Biol. 401–11 (1992); R. P. Skoff, The Lineages of Neuroglial Cells, 2 The Neuroscientist 335–44 (1996). These cells, often referred to as neuroepithelial stem cells (NEP cells), have the capacity to undergo self renewal and to differentiate into neurons, oligodendrocytes, and astrocytes, thus representing multipotent stem cells. A. A. Davis & S. Temple, A Self-Renewing Multipotential Stem Cell in Embryonic Rat Cerebral Cortex, 362 Nature 363–72 (1994); A. G. Gritti et al., Multipotential Stem Cells from the Adult Mouse Brain Proliferate and Self-Renew in Response to Basic Fibroblast Growth Factor, 16 J. Neurosci. 1091–1100 (1996); B. A. Reynolds et al., A Multipotent EGF-Responsive Striatal Embryonic Progenitor Cell Produces Neurons and Astrocytes, 12 J. Neurosci. 4565–74 (1992); B. A. Reynolds & S. Weiss, Clonal and Population Analyses Demonstrate that an EGF-Responsive Mammalian Embryonic CNS Precursor is a Stem Cell, 175 Developmental Biol. 1–13 (1996); B. P. Williams et al., The Generation of Neurons and Oligodendrocytes from a Common Precursor Cell, 7 Neuron 685–93 (1991).

The nervous system also contains precursor cells with restricted differentiation potentials. T. J. Kilpatrick & P. F. Bartlett, Cloned Multipotential Precursors from the Mouse Cerebrum Require FGF-2, Whereas Glial Restricted Precursors are Stimulated with Either FGF-2 or EGF, 15 J. Neurosci. 3653–61 (1995); J. Price et al., Lineage Analysis in the Vertebrate Nervous System by Retrovirus-Mediated Gene Transfer, 84 Developmental Biol. 156–60 (1987); B. A. Reynolds et al., supra; B. A. Reynolds & S. Weiss, supra; B. Williams, Precursor Cell Types in the Germinal Zone of the Cerebral Cortex, 17 BioEssays 391–93 (1995); B. P. Williams et al., supra. The relationship between multipotent stem cells and lineage restricted precursor cells is still unclear. In principal, lineage restricted cells could be derived from multipotent cells, but this is still a hypothetical possibility in the nervous system with no direct experimental evidence. Further, no method of purifying such precursors from multipotent cells has been described.

As has been shown in copending U.S. patent application Ser. No. 08/852/744, entitled "Generation, Characterization, and Isolation of Neuroepithelial Stem Cells and Lineage Restricted Intermediate Precursor," filed May 7, 1997, now U.S. Pat. No. 5,361,996, hereby incorporated by reference in its entirety, NEP cells grow on fibronectin and require fibroblast growth factor (FGF) and an as yet uncharacterized component present in chick embryo extract (CEE) to proliferate and maintain an undifferentiated phenotype in culture. The growth requirements of NEP cells are different from neurospheres isolated from E14.5 cortical ventricular zone cells. B. A. Reynolds et al., supra; B. A. Reynolds & S. Weiss, supra; WO 9615226; WO 9615224; WO 9609543; WO 9513364; WO 9416718; WO 9410292; WO 9409119. Neurospheres grow in suspension culture and do not require CEE or FGF, but are dependent on epidermal growth factor (EGF) for survival. FGF itself is not sufficient for long term growth of neurospheres, though FGF may support their growth transiently. NEP cells, however, grow in adherent culture, are FGF dependent, do not express detectable levels of EGF receptors, and are isolated at a stage of embryonic development prior to which it has been possible to isolate neurospheres. Thus, NEP cells may represent a multipotent precursor characteristic of the brain stem and spinal cord, while neurospheres may represent a stem cell more characteristic of the cortex. Nonetheless, NEP cells provide a model system for studying the principles of lineage restriction from multipotent stem cells or precursor cells of the central nervous system. The principles elucidated from the study of NEP cells are expected to be broadly applicable to all CNS precursor cells sufficiently multipotent to generate both neurons and glia. Thus, the present application is intended to be applicable to any CNS precursor cells regardless of their site of derivation as long as they are able to differentiate to both neurons and glial cells.

U.S. Pat. No. 5,589,376, to D. J. Anderson and D. L. Stemple, discloses mammalian neural crest stem cells and methods of isolation and clonal propagation thereof, but fails to disclose cultured NEP cells, cultured lineage restricted precursor cells, and methods of generating, isolating, and culturing thereof. Neural crest cells differentiate into neurons and glia of the peripheral nervous system (PNS), whereas the neuroepithelial stem cells differentiate into neurons and glia of the central nervous system (CNS).

The neuron-restricted precursor cells described herein are distinct from the NEP cells, neurospheres, and neural crest stem cells that have been described elsewhere. NEP cells are capable of differentiating into neurons or glia whereas NRP's can differentiate into neurons, but not glia, and NEP cells and NRP's display distinct cell markers. As mentioned above, neurospheres grow in suspension culture and do not require CEE or FGF, but are dependent on EGF for survival, whereas NRP cells grow in adherent culture and do not express detectable levels of EGF receptors. Further, neural crest cells differentiate into neurons and glia of the peripheral nervous system (PNS), whereas NRP cells differentiate into neurons of the central nervous system (CNS). NRP cells express polysialated or embryonic neural cell adhesion molecule (E-NCAM), but NEP cells, neurospheres, and neural crest cells do not. Therefore, NRP cells are different in their proliferative potential, expression of cell markers, and nutritional requirements from these other cell types.

The ability to isolate and grow mammalian neuronal-restricted precursor cells in vitro allows for of using pure populations of neurons for transplantation, discovery of genes specific to selected stages of development, generation of cell-specific antibodies for therapeutic and diagnostic uses such as for targeted gene therapy, and the like. Further, NRP cells can be used to generate subpopulations of neurons with specific properties, i.e. motoneurons and other neuronal cells for analyzing neurotransmitter functions and small molecules in high throughput assays. Moreover, the methods of obtaining NRP cells from NEP cells provides for a ready source of a large number of post-mitotic neurons. Post-mitotic cells obtained from a tumor cell line are already being commercially marketed (e.g., Clontech, Palo Alto, Calif.). The present invention is also necessary to understand how multipotent neuroepithelial stem cells become restricted to the various neuroepithelial derivatives. In particular, culture conditions that allow the growth and self-renewal of mammalian neuronal-restricted precursor cells are desirable so that the particulars of the development of these mammalian stem cells can be ascertained. This is desirable because a number of tumors of neuroepithelial derivatives exist in mammals, particularly humans. Knowledge of mammalian neuroepithelial stem cell development is therefore needed to understand these disorders in humans.

In view of the foregoing, it will be appreciated that isolated populations of mammalian lineage restricted neuronal precursor cells and methods of generating, isolating, and culturing such cells would be significant advancements in the art.

BRIEF SUMMARY OF THE INVENTION

It is an object of the present invention to provide isolated (pure) populations of mammalian neuronal-restricted precursor cells and their progeny.

It is another object of the invention to provide methods of generating, isolating, culturing, and regenerating of mammalian lineage-restricted neuronal precursor cells and their progeny.

It is yet another object of the invention to provide a method for the generation of lineage-restricted neuronal precursor cells from and CNS multipotent precursor cell able to generate both neurons and glia.

It is a still further object of the invention to provide pure differentiated populations of neuronal cells derived from lineage-restricted neuronal precursor cells.

These and other objects can be achieved by providing an isolated, pure population of mammalian CNS neuron-restricted precursor cells. Preferably, such neuron-restricted precursor cells are capable of self-renewal, differentiation to CNS neuronal cells but not to CNS glial cells, and expressing embryonic neural cell adhesion molecule, but not expressing a ganglioside recognized by A2B5 antibody. These neuron-restricted precursor cells may or may not express nestin or β-III tubulin. Thus, embryonic neural cell adhesion molecule is a defining antigen for these cells.

A method of isolating a pure population of mammalian CNS neuron-restricted precursor cells comprises the steps of:
  (a) isolating a population of mammalian multipotent CNS stem cells capable of generating both neurons and glia;
  (b) incubating the multipotent CNS stem cells in a medium configured for inducing the cells to begin differentiating;
  (c) purifying from the differentiating cells a subpopulation of cells expressing a selected antigen defining neuron-restricted precursor cells; and
  (d) incubating the purified subpopulation of cells in a medium configured for supporting adherent growth thereof.

In a preferred embodiment of this method, the selected antigen defining neuron-restricted precursor cells is embryonic neural cell adhesion molecule. The purification of the subpopulation of cells expressing the defining antigen can be by specific antibody capture, fluorescence activated cell sorting, magnetic bead capture, or any equivalent methods that isolate the cells expressing the defining antigen. Specific antibody capture, fluorescence activated cell sorting, and magnetic bead capture, as well as other equivalent methods, are well known in the art. Specific antibody capture is a preferred procedure for purifying such cells. In one preferred embodiment, the mammalian multipotent CNS stem cells are neuroepithelial stem cells.

Another method of isolating a pure population of mammalian CNS neuron-restricted precursor cells comprises the steps of:
  (a) removing a sample of CNS tissue from a mammalian embryo at a stage of embryonic development after closure of the neural tube but prior to differentiation of glial and neuronal cells in the neural tube;
  (b) dissociating cells comprising the sample of CNS tissue removed from the mammalian embryo;
  (c) purifying from the dissociated cells a subpopulation expressing a selected antigen defining neuron-restricted precursor cells;
  (d) plating the purified subpopulation of cells in feeder-cell-independent culture on a substratum and in a medium configured for supporting adherent growth of the neuron-restricted precursor cells; and
  (e) incubating the plated cells at a temperature and in an atmosphere conducive to growth of the neuron-restricted precursor cells.

In a preferred embodiment of this method, the selected antigen defining neuron-restricted precursor cells is embryonic neural cell adhesion molecule. As described above, purification of the subpopulation of cells expressing a defining antigen can be by methods well known in the art, such as specific antibody capture, fluorescence activated cells sorting, and magnetic bead capture, and the like. Specific antibody capture is preferred.

A method of obtaining postmitotic neurons comprises:
  (a) providing neuron-restricted precursor cells and culturing the neuron-restricted precursor cells in proliferating conditions; and
  (b) changing the culture conditions of the neuron-restricted precursor cells from proliferating conditions to differentiating condition, thereby causing the neuron-restricted precursor cells to differentiate into postmitotic neurons. Changing the culture conditions can comprise adding retinoic acid to the basal medium, withdrawing a mitotic factor (such as fibroblast growth factor) from the basal medium, or adding a neuronal maturation factor (such as sonic hedgehog and brain-derived neurotrophic factor) to the basal medium.

DETAILED DESCRIPTION

Before the present neuronal-restricted precursor cells and methods of making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof It must be noted that, as used in this specification and the appended claims, the singular forms "a," "an," and "the"

include plural referents unless the context clearly dictates otherwise. Thus, for example, reference to "an embryo" includes reference to two or more embryos, reference to "a mitogen" includes reference to a mixture of two or more mitogens, and reference to "a factor" includes reference to a mixture of two or more factors.

In describing and claiming the present invention, the following terminology will be used in accordance with the definitions set out below.

As used herein, "self renewal" refers, for example, to the capability of a neuroepithelial stem cell to divide to produce two daughter cells, at least one of which is a multipotent neuroepithelial stem cell, or to the capability of a neuronal-restricted precursor cell to divide to produce two daughter cells, at least one of which is a neuronal-restricted precursor cell.

As used herein, "clonal density" and similar terms mean a density sufficiently low enough to result in the isolation of single, non-impinging cells when plated in a selected culture dish. An illustrative example of such a clonal density is about 225 cells/100 mm culture dish.

As used herein, "feeder-cell-independent adherent culture" and similar terms mean the growth of cells in vitro in the absence of a layer of different cells that generally are first plated on a culture dish to which the cells from the tissue of interest are then added. In feeder cell cultures, the feeder cells provide a substratum for the attachment of cells from the tissue of interest and additionally serve as a source of mitogens and survival factors. The feeder-cell-independent adherent cultures herein use a chemically defined substratum, for example fibronectin, and mitogens or survival factors are provided by supplementation of the liquid culture medium with either purified factors or crude extracts from other cells or tissues. Therefore, in feeder-cell-independent cultures, the cells in the culture dish are primarily cells derived from the tissue of interest and do not contain other cell types required to support the growth of cells derived from the tissue of interest.

As used herein, "effective amount" means an amount of a growth factor or survival factor or other factor that is nontoxic but sufficient to provide the desired effect and performance. For example, an effective amount of FGF as used herein means an amount selected so as to support self renewal and proliferation of NEP cells when used in combination with other essential nutrients, factors, and the like.

The present invention is illustrated using neuron-restricted precursor cells isolated from the rat. The invention, however, encompasses all mammalian neuronal-restricted precursor cells and is not limited to neuronal-restricted precursor cells from the rat. Mammalian neuron-restricted precursor cells can be isolated from human and non-human primates, equines, canines, felines, bovines, porcines, ovines, lagomorphs, and the like.

Pluripotent stem cells in the central nervous system may generate differentiated neurons and glia either directly or through the generation of lineage-restricted intermediate precursors. In the developing retina, it appears that multipotent retinal precursors can generate any combination of differentiated cells even at their final division, indicating that intermediate precursors do not exist. In other regions of the central nervous system, in contrast, retroviral labeling studies have suggested the existence of lineage-restricted precursors that generate only one type of cell or a limited number of cell types. Intermediate stage precursors such as the bipotential oligodendrocyte-type-2-astrocyte precursor (O-2A) and a neuronal precursor have also been described in tissue culture studies. Yet, the generation of intermediate lineage-restricted precursors from pluripotent embryonic or adult stem cells or other stem cells capable of differentiating into neurons and glia has not been observed. Thus, the lineal relationship between pluripotent stem cells identified in culture and the committed precursors identified in vivo and in vitro has heretofore been unknown. Possible models of development have included (1) pluripotent and more committed stem cells representing lineally related cells or (2) such cells representing independent pathways of differentiation.

The developing spinal cord represents an ideal model for studying this differentiation. At embryonic day 10.5 (E10.5), the caudal neural tube appears as a homogeneous population of nestin-immunoreactive dividing cells in vivo and in vitro. These initially homogeneous cells are patterned over several days to generate neurons, oligodendrocytes, and astrocytes in a characteristic spatial and temporal profile. Neurogenesis occurs first on a ventro-dorsal gradient, with the earliest neurons becoming postmitotic on E13.5 in rats. Neurogenesis continues over an additional two days followed by differentiation of oligodendrocyte precursors and the subsequent differentiation of astrocytes.

Methods for growing neuroepithelial stem (NEP) cells isolated from E10.5 rat embryos as undifferentiated cells for extended periods in vitro have been described in Ser. No. 08/852,744, and it has been shown further that these populations were able to generate the three major cell types in the CNS. Thus, NEP cells represent a dividing multipotent stem cell that may differentiate into neurons either via an intermediate neuroblast or directly as a part of its terminal differentiation. To determine whether neurons differentiated from NEP cells via intermediate, more-restricted precursors, a variety of immunologically defined populations from differentiating cultures of NEP cells were isolated and characterized. It is shown herein that cells morphologically and phenotypically identical to NRP's can be isolated from NEP cell cultures. Clonal analysis shows that individual NEP cells generate neurons via the generation of neuronal precursors and that individual NEP cells can generate neuron-restricted and glial-restricted precursors. It is further shown that E-NCAM$^+$(embryonic neural cell adhesion molecule positive) cells are present in E13.5 neural tube cultures and that these cells are mitotic, self renewing stem cells that can generate multiple neuronal phenotypes, but not astrocytes or oligodendrocytes. Thus, neuron restricted precursors (NRP's) are an identifiable stage in the in vivo differentiation of neurons. These data provide a demonstration of a direct lineal relationship between multipotent and neuron-restricted stem cells and suggest that neural differentiation involves progressive restriction in developmental fate.

FIG. 1 presents a model for spinal cord differentiation. This model is similar to that proposed for hematopoiesis and for differentiation of neural crest (see review by D. J. Anderson, The Neural Crest Lineage Problem: Neuropoiesis?, 3 Neuron 1–12 (1989)). According to this model, NEP cells 10 represent a homogeneous population of cells in the caudal neural tube that express nestin (i.e. nestin$^+$) but no other lineage marker (lin$^-$). These cells divide and self renew in culture and generate differentiated phenotypes. Previous data have suggested intermediate dividing precursors with a more restricted potential. R. H. Miller & V. Szigeti, infra; B. C. Warf et al., supra; N. P. Pringle & W. D. Richardson, supra; J. Ray & F. Gage, Spinal Cord Neuroblasts Proliferate in Response to Basic Fibroblast Growth Factor, 14 J. Neurosci. 3548–64 (1994). Such precursors include those precursors 14 that generate oligodendrocytes and type 2 astrocytes, bipotent astrocyte and neuronal precursors (not shown in FIG. 1), as well as neuronal progenitors 18 that generate several kinds of neurons 22, 26, 30. The model therefore suggests that the multipotent precursors (NEP cells) generate differentiated cells (i.e., oligodendrocytes, type 2 astrocytes, type 1 astrocytes, neurons, and motoneurons) through intermediate precursors. Consistent with this model are the results presented herein showing the existence of cells with a neuron-restricted proliferative potential.

NEP cell cultures provide a large source of transient cells that can be sorted to obtain differentiated cell types. The results described herein provide direct evidence to support a model describing initially multipotent cells undergoing progressive restriction in developmental potential under extrinsic influence to generate the different phenotypes within the CNS. Evidence is provided that initially multipotent NEP cells generate neuron-restricted precursors in vitro and that such neuron-restricted precursors are also present in vivo. It is also shown that NRP's fulfill criteria of blast cells and that a direct lineal relationship between multipotent stem cells and more restricted NEP cells exists.

The results presented herein support that E-NCAM-immunoreactive cells are restricted in their developmental potential. E-NCAM$^+$ cells fail to differentiate into oligodendrocytes or astrocytes under any culture conditions tested. In contrast, NEP cells differentiate into neurons, astrocytes, and oligodendrocytes, and A2B5-immunoreactive cells differentiate into oligodendrocytes under identical conditions. For these reasons, E-NCAM-immunoreactive cells are described herein as neuron-restricted precursors or NRP's.

Immunopanning and double-labeling data demonstrate that E-NCAM can be used to identify a specific neuronal sublineage that is generated from multipotential NEP cells. Like markers for intermediate precursors in the hematopoietic system and neural crest, however, E-NCAM, and the A2B5 glial precursor marker as well, is not unique to intermediate precursors. E-NCAM has been shown to label some astrocytes. Similarly, A2B5 has been shown to recognize neurons in some species and is transiently expressed by astrocytes in some culture conditions. Nevertheless, under the specific culture conditions defined herein these markers can be used to select intermediate precursors and therefore represent the first cell surface epitopes that are co-expressed in concordance with a restriction in developmental potential.

The basal medium (NEP medium) used in the experiments described herein comprises DMEM-F12 (GIBCO/BRL, Gaithersburg, Md.) supplemented with 100 μg/ml transferrin (Calbiochem, San Diego, Calif.), 5 μg/ml insulin (Sigma Chemical Co., St. Louis, Mo.), 16 gig/ml putrescine (Sigma), 20 nM progesterone (Sigma), 30 nM selenious acid (Sigma), 1 mg/ml bovine serum albumin (GIBCO/BRL), plus B27 additives (GIBCO/BRL), 20 ng/ml basic fibroblast growth factor (bFGF), and 10% chick embryo extract (CEE). In general, these additives were stored as 100X concentrates at −20° C. until use. Normally, 200 ml of NEP medium was prepared with all additives except CEE and used within two weeks of preparation. CEE was added to the NEP medium at the time of feeding cultured cells.

FGF and CEE were prepared as described in D. L. Stemple & D. J. Anderson, supra; M. S. Rao & D. J. Anderson, supra; L. Sommers et al., Cellular Function of the bHLH Transcription Factor MASH1 in Mammalian Neurogenesis, 15 Neuron 1245–58 (1995), hereby incorporated by reference. FGF is also available commercially (UBI).

Briefly, CEE was prepared as follows. Chick eggs were incubated for 11 days at 38° C. in a humidified atmosphere. Eggs were washed and the embryos were removed and placed in a petri dish containing sterile Minimal Essential Medium (MEM with glutamine and Earle's salts) (GIBCO/BRL) at 4° C. Approximately 10 embryos each were macerated by passage through a 30-ml syringe into a 50-ml test tube. This procedure typically produced about 25 ml of medium. To each 25 ml was added 25 ml of MEM. The tubes were rocked at 4° C. for 1 hour. Sterile hyaluronidase (1 mg/25 g of embryo) (Sigma) was added, and the mixture was centrifuged for 6 hours at 30,000 g. The supernate was collected, passed through a 0.45 μm filter and then through a 0.22 μm filter, and stored at −80° C. until use.

Laminin (Biomedical Technologies Inc.) was dissolved in distilled water to a concentration of 20 mg/ml and applied to tissue culture plates (Falcon). Fibronectin (Sigma) was resuspended to a stock concentration of 10 mg/ml and stored at −80° C. and then diluted to a concentration of 250 μg/ml in D-PBS (GIBCO/BRL). The fibronectin solution was applied to tissue culture dishes and immediately withdrawn. Subsequently, the laminin solution was applied and plates were incubated for 5 hours. Excess laminin was withdrawn, and the plates were allowed to air dry. Coated plates were then rinsed with water and allowed to dry again. Fibronectin was chosen as a growth substrate for NEP cells because NEP cells did not adhere to collagen or poly-L-lysine (PLL) and adhered poorly to laminin. Thus, all subsequent experiments to maintain NEP cells in culture were performed on fibronectin-coated dishes. Laminin-coated dishes were used, however, to promote differentiation of NEP stem cells.

For clonal analysis, cells harvested by trypsinization were plated at a density of 50–100 cells per 35 mm dish. Individual cells were identified and located on the dish by marking the position with a grease pencil. Cells were grown in DMEM/F12 with additives, as described above, for a period ranging from 10–15 days.

EXAMPLE 1

To determine if a dividing neuron-restricted precursor is normally present in vivo, sections of E13.5 rat spinal cords were analyzed with a panel of early neuronal markers. Sections were cut of embryos fresh frozen at 13.5 days gestation and then were labeled by immunocytochemistry. Staining procedures were carried out according to methods well known in the art. Cells were double-labeled with antibodies against E-NCAM (Developmental Studies Hybridoma Bank, Iowa) and β-III tubulin (Sigma Chemical Co., St. Louis, Mo.) or were stained with E-NCAM and counterstained with DAPI, a nuclear marker for identifying all cells. All secondary monoclonal antibodies were from Southern Biotechnology.

Polysialated or embryonic N-CAM (E-NCAM) appeared to be a likely marker for neuronal precursors. E-NCAM immunoreactivity was first detected at E13.5. E-NCAM immunoreactive cells could be seen in the margins of the neural tube, but not in the proliferating ventricular zone. Double-labeling with β-III tubulin indicated that most E-NCAM-immunoreactive cells co-expressed this neuronal marker. A small proportion of cells present more medially were E-NCAM$^+$, but did not express β-III tubulin immunoreactivity, suggesting that E-NCAM may be an early and specific marker of differentiation into neuronal precursors that is expressed prior to βIII tubulin.

EXAMPLE 2

To characterize E-NCAM-immunoreactive cells, E13.5 spinal cords were dissociated and E-NCAMimmunoreactive cells were stained with a panel of antibodies (Table 1). Sprague-Dawley rat embryos were removed at embryonic day 13.5 and placed in a petri dish containing Hanks balanced salt solutions (HBSS, Gibco). The trunk segments of the embryos were dissected using tungsten needles, rinsed, and then transferred to fresh HBSS. Spinal cords were mechanically dissected free from the surrounding connective tissue using sharpened No. 5 forceps. Isolated spinal cords were incubated in 0.05% trypsin/EDTA solution for 20 minutes. The trypsin solution was replaced with fresh HBSS containing 10% fetal bovine serum (FBS). The segments were gently triturated with a Pasteur pipette to dissociate cells. Cells dissociated by trituration were plated in PLL/1aminin-coated 35 mm dishes (Nunc) at high density and stained after 24 hours.

TABLE 1

| Antibody/Kind | Source | Antigen Recognized | Cell Type Recognized |
| --- | --- | --- | --- |
| Anti-NCAM/mouse IgG | DSHB[a] | Polysialated N-CAM | Neurons |
| Anti-Nestin | DSHB | Nestin | NEP cells |
| Anti-β-III tubulin/ mouse IgG1 | Sigma[b] | Intermediate filament | Neurons |
| RT-97 | DSHB | Neurofilaments | Neurons |
| Anti-A2B5/mouse IgM | BMB[c] | Ganglioside | Oligodendrocytes and precursors |
| Anti-GFAP/rabbit IgG | Accurate[d] | Glial fibrillary acid | Astrocytes |
| Anti-NF60 | Chemicon[e] | Neurofilament 60 | Neurons |
| Anti-GalC/mouse IgG | BMB | Galacto-cerebroside | Oligodendrocytes and precursors |
| Anti-Peripherin | Chemicon | Peripherin | Motoneurons, PNS Neurons |
| Anti-MAP kinase | Chemicon | MAP2 kinase | Neurons |

[a]Developmental Studies Hybridoma Bank, Iowa
[b]Sigma Chemical Co., St. Louis, MO
[c]Boehringer Mannheim Biochemicals, Gaithersburg, MD
[d]Accurate, Westbury, NY
[e]Chemicon, Temecula, CA Staining for the cell surface markers, such as A2B5 and α-GalC, was carried out with cultures of living cells. To stain cells with antibodies against internal antigens such as GFAP, which specifically recognizes astrocytes (A. Bignami et al., Localization of the Glial Fibrillary Acidic Protein in Astrocytes, by Immunofluorescence, 43 Brain Res. 429–35 (1972)), β-III tubulin (DAKO) and RT-97, which stain neurons (E. Geisert & A. Frankfurter, The Neuronal Response to Injury as Visualized by Immunostaining of Class β-tubulin in the Rat, 102 Neurosci. Lett. 137–41 (1989), nestin, which is a marker for undifferentiated stem cells (U. Lendahl et al., CNS Stem Cells Express a New Class of Intermediate Filament Protein, 60 Cell 585–95 (1990)), or 5-bromodeoxyuridine (BrdU, Sigma), which is a marker for determining the number of dividing cells, cultures were fixed in ice-cold methanol. Double- or triple-labeling experiments were performed by simultaneously incubating cells in appropriate combinations of primary antibodies followed by non-cross-reactive secondary antibodies, , e.g. M. Mayer et al., Ciliary Neurotrophic Factor and Leukemia Inhibitory Factor Promote the Generation, Maturation, and Survival of Oligodendrocytes, 120 Development 142–53 (1994), hereby incorporated by reference. In triple-label experiments, cultures were incubated with the primary antibody in blocking buffer for a period of 1 hour, rinsed with PBS, and incubated with a species-specific secondary antibody in blocking buffer for 1 hour. Cultures were rinsed three times with PBS and examined under a fluorescence microscope. For labeling with 4 antibodies simultaneously, live cells were first incubated with the surface antibodies A2B5 and α-GalC without the secondary layers. Cells were then fixed in ice-cold methanol for ten minutes and stained with α-β-III tubulin and the appropriate secondary antibody. After scoring the results of this staining, which was usually negative, clones were stained with GFAP and the secondary layer for the first set of surface antibodies. Finally, the secondary antibody for GFAP was added. This procedure allowed staining with four antibodies using only three fluorescent-color conjugated secondary antibodies.

E-NCAM-immunoreactive cells constituted 60%±3% of all cells present in dissociated culture 24 hours after plating. The majority of the remaining cells were A2B5. It has been shown in Ser. No. 08/852,944, now U.S. Pat. No. 6,361,996, that at this stage of development, A2B5-immunoreactive cells are glial precursor cells. Consistent with these results, β-III tubulin or E-NCAM-immunoreactive cells did not co-express A2B5. The vast majority of cultured E-NCAM-immunoreactive cells (85%±8%) co-expressed β-III tubulin immunoreactivity as well as nestin immunoreactivity, but not markers characteristic of glial precursor immunoreactivity. Approximately 20% of the E-NCAM$^+$ cells is divided in a 24-hour period. Most of the dividing E-NCAM$^+$ cells did not co-express β-III tubulin, indicating that this population of cells could represent a dividing neuroblast. It is not yet known whether a higher percentage of the cells would be observed to divide under these conditions with longer labeling periods. However, even if this population were to include a subset of cells sufficiently committed to neuronal differentiation as to no longer engage in division, these committed neurons would be eliminated from the population with expansion and division in tissue culture. Table 2 summarizes results of the antigenic profile of the cells, showing the percentages of E-NCAM$^+$ cells from E13.5 embryos that express various other antigens. These results show that E-NCAM$^+$ cells from E13.5 spinal cord express neuronal, but not glial, markers.

TABLE 2

| Antigen | % Expression |
| --- | --- |
| α-Nestin | 98% |
| α-β-III tubulin | 50% |
| RT-97 | 95% |
| α-NF M | 100% |
| α-MAP kinase | 100% |
| A2B5 | 0% |
| α-GFAP | 0% |
| α-NF 60 | 0% |
| α-GalC | 0% |
| α-Peripherin | 0% |

EXAMPLE 3

To determine the differentiation potential of E-NCAM-immunoreactive cells, E-NCAM$^+$ cells were purified by immunopanning and plated at clonal density in gridded dishes. E13.5 cells were prepared according to the procedure of Example 2. An E-NCAM$^+$ cell population was purified from these E13.5 cells using a specific antibody-capture technique according to the procedure of L. Wysocki & V. Sato, "Panning" for Lymphocytes: A Method for Cell Selection, 75 Proc. Nat'l Acad. Sci. USA 2844–48 (1978); M. Mayer et al., supra, hereby incorporated by reference. In brief, cells were trypsinized and the resulting cell suspension was plated on an A2B5-antibody-coated dish to allow binding of all A2B5⁺ cells to the plate. The supernate was removed, and the plate was washed with DMEM supplemented with additives described by J. Bottenstein and G. Sato, Growth of a Rat Neuroblastoma Cell Line in Serum-free Supplemented Medium, 76 Proc. Nat'l Acad. Sci. USA 514–17 (1979), hereby incorporated by reference, (DMEM-BS). The supernate was then plated on an E-NCAM-antibody-coated dish to allow binding of the E-NCAM-immunoreactive cells. The bound cells were scraped from the plate and replated on fibronectin/laminin-coated glass coverslips in 300 ml DMEM-BS±growth factors at 5000 cells/well.

The A2B5 and E-NCAM antibodies for coating the plates were used at concentrations of 5 µg/ml. Cells were allowed to bind to the plate for 20–30 minutes in a 37° C. incubator. Growth factors were added every other day at a concentration of 10 ng/ml. Recombinant bFGF and neurotrophin 3 (NT-3) were purchased from PeproTech, and retinoic acid (RA) was obtained from Sigma.

After 24 hours, some immunopanned E-NCAM⁺ cells were assayed by immunocytochemistry according to the procedure of Example 2. Greater than 95% of the cells were E-NCAM⁺ at that time. Purified and stained cells were plated on gridded clonal dishes, and individual E-NCAM⁺ cells were identified and followed over time by immunocytochemistry according to the procedure of Example 2.

Of all the cytokines tested, optimum growth was observed when cells were cultured in FGF (10 ng/ml) and NT-3 (10 ng/ml). In the presence of FGF and NT-3, single E-NCAM⁺ cells divided in culture to generate colonies ranging from one to several hundred cells. By day 5, most colonies contained between 20 and 50 daughter cells that continued to express E-NCAM immunoreactivity. Daughter cells appeared phase bright and had short processes. At this stage, most E-NCAM-positive cells did not express β-III tubulin or neurofilament-M immunoreactivity.

To promote differentiation of E-NCAM⁺ clones, the FGF- and NT-3-containing medium was replaced with medium containing retinoic acid (RA) and from which the mitogen, bFGF, was withheld. In this differentiation medium, E-NCAM⁺ cells stopped dividing and elaborated extensive processes and started to express neuronal markers. Quadruple-labeling of clones with neuronal and glial markers and DAPI histochemistry, to identify all cells, showed that all clones contained β-III tubulin-immunoreactive cells and NF-M-immunoreactive cells and that none of the E-NCAM⁺ clones differentiated into oligodendrocytes or astrocytes.

Table 3 summarizes the results obtained by quadruple labeling of 124 E-NCAM⁺ clones with DAPI, α-β-III tubulin, A2B5, and α-GFAP.

TABLE 3

| Antigen Expressed | % of Clones |
| --- | --- |
| α-β-III tubulin | 100% |
| A2B5 | 0% |
| α-GFAP | 0% |

EXAMPLE 4

In this example, immunopanned A2B5⁺ cells derived from dissociated E13.5 spinal cords according to the procedure of Example 2 were cultured in neuron-promoting medium, i.e. basal medium plus FGF and NT-3. Cultures were grown for 5 days and then switched to RA-containing medium as described in Example 3, and sister plates were stained for either E-NCAM or A2B5 immunoreactivity.

No A2B5 immunopanned cell expressed E-NCAM immunoreactivity when grown under conditions that promote growth of neuronal cells. All A2B5 immunopanned cells, however, continued to express A2B5 immunoreactivity, indicating that neuron-promoting conditions do not affect the survival and proliferation of glial precursor cells. Thus, the inability to detect oligodendrocyte and astrocyte differentiation in Example 3 was unlikely to be due to the death in neuronal cultures of oligodendrocytes and astrocytes that might have differentiated from E-NCAM⁺ precursors since A2B5 glial precursor cells purified and grown in parallel in the presence of FGF and NT-3 continued to express A2B5 without apparent cell death and generated healthy oligodendrocytes and astrocytes after 10 days in culture. In addition, A2B5⁺ cells never generated neurons in the presence of FGF and NT-3 and showed no expression of E-NCAM at any time tested. Thus, E-NCAM immunoreactive cells, unlike A2B5-immunoreactive glial restricted precursors, could not differentiate into oligodendrocytes and appeared limited to neuronal differentiation when compared to multipotential E10.5 neuroepithelial cells.

EXAMPLE 5

While it has been clearly shown in the present system that E-NCAM identifies neuronally restricted precursor cells, it has been reported that certain glial precursors at later stages of development can also express E-NCAM immunoreactivity. This observation raises the possibility that some E-NCAM⁺ cells identified by the presently described methods may be bi-potential. To test this possibility, E-NCAM⁺ cells were plated clonally in either neuron-promoting medium (FGF+NT-3) or in glial-promoting medium (FGF+10% fetal calf serum) and compared for their development. Medium containing FGF with 10% fetal calf serum was chosen for glial differentiation since this medium promotes astrocyte differentiation of both spinal cord NEP cells as well as A2B5 immunoreactive A2B5 glial precursor cells, as shown in Ser. No. 08/852,744, now U.S. Pat. No. 6,361,996. All E-NCAM⁺ clones (24/24) that were grown in neuron-promoting medium contained only β-III tubulin⁺ cells after 8 days, while the clones grown in serum-containing medium did not generate astrocytes or proliferate. From a total of 97 E-NCAM⁺ cells grown in glial-promoting conditions, 90 clones (92%) consisted of a single dead cell after 24 hours, while the remaining 7 clones (8%) contained 1 or 2 dead cells after 48 hours. Thus, E-NCAM immunoreactive cells, in contrast with glial precursor cells, fail to proliferate or differentiate in astrocyte-promoting conditions.

EXAMPLE 6

To determine whether the restriction of E-NCAM⁺ cells to generation of neurons also includes a restriction to generation of certain subtypes of neurons, E-NCAM⁺ clones grown in RA and NT-3 in the absence of FGF were examined for the expression of different neurotransmitters. The antibodies used in this example are described in Table 4.

TABLE 4

| Antibody/Kind | Source | Antigen Recognized | Cell Type Recognized |
| --- | --- | --- | --- |
| Anti-ChAT/goat IgG | Chemicon | Choline acetyl transferase | Motoneurons |
| Anti-Glutamate/rabbit IgG | Chemicon | Glutamate | Excitatory neurons |
| Anti-GABA/rabbit IgG | Chemicon | Gamma amino butyric acid | Inhibitory neurons |

These results indicate that individual clones could generate GABA-ergic, glutaminergic, and cholinergic neurons. Of ten clones tested, all contained glutaminergic, GABAergic, and cholinergic neurons. Thus, E-NCAM-immunoreactive cells, while limited to differentiating neurons, are capable of generating excitatory, inhibitory, and cholinergic neurons.

EXAMPLE 7

Primary clones of E-NCAM$^+$ cells grown in FGF and NT-3 according to the procedure of Example 5 grew to large sizes of several hundred cells after 7 to 10 days in culture, indicating some degree of self renewal. To demonstrate prolonged self renewal of the E-NCAM$^+$ population, selected clones were followed by secondary and tertiary subcloning. Individual E-NCAM$^+$ cells from E13.5 spinal cord were plated in fibronectin/laminin and expanded for 7 days in the presence of FGF and NT-3. Five individual clones were randomly selected and replated at clonal density using the same expansion conditions. The number of secondary clones was counted, and large clones were selected and replated. The number of tertiary clones obtained was counted, and clones were then induced to differentiate into postmitotic neurons by replacing FGF and RA.

All clones examined generated numerous daughter clones that subsequently generated tertiary clones. Small clones and very large clones showed similar self renewal potential. When tertiary clones were switched to a medium containing RA and lacking FGF, the majority of cells in a clone differentiated into post-mitotic neurons expressing β-III tubulin. Thus, E-NCAM$^+$ cells are capable of prolonged self renewal and can generate multiple daughter cells capable of generating neurons.

These results suggest that E-NCAM immunoreactivity identifies a neuroblast cell that can differentiate into multiple neuronal phenotypes in culture, even after multiple passages. NT-3 and FGF are required to maintain the blast cell in a proliferative state, while RA promotes differentiation.

EXAMPLE 8

It has been shown previously that individual NEP cells derived from E10.5 spinal cord are an E-NCAM-immunonegative, multipotent, self renewing population of cells that can generate neurons, astrocytes, and oligodendrocytes (Ser. No. 08/852,744, now U.S. Pat. No. 6,361, 996). To determine if neuronal differentiation from NEP precursors involved the generation of an E-NCAM$^+$ intermediate neuronal precursor cell, NEP cell cultures that were induced to differentiate in vitro were examined for the presence of E-NCAM$^+$ immunoreactive cells.

NEP cells were prepared according to the method described in Ser. No. 08/852,744, now U.S. Pat. No. 6,361, 996. Briefly, Sprague Dawley rat embryos were removed at E10.5 (13–22 somites) and placed in a petri dish containing Ca/Mg-free Hanks balanced salt solution (HBSS, GIBCO/BRL). The trunk segments of the embryos (last 10 somites) were dissected using tungsten needles, rinsed, and then transferred to fresh HBSS. Trunk segments were incubated at 4° C. in 1% trypsin solution (GIBCO/BRL) for a period of ten to twelve minutes. The trypsin solution was replaced with fresh HBSS containing 10% fetal bovine serum (FBS, GIBCO/BRL). The segments were gently triturated with a Pasteur pipette to release neural tubes free from surrounding somites and connective tissue. Isolated neural tubes were transferred to a 0.05% trypsin/EDTA solution (GIBCO/BRL) for an additional period of ten minutes. Cells were dissociated by trituration and plated at high density in 35 mm fibronectin-oated dishes in NEP medium. Cells were maintained at 37° C. in 5% $CO_2$/95% air. Cells were replated at low density, i.e. ≦5000 cells per 35 mm plate, one to three days after plating. Cells from several dishes were then harvested by trypsinization (0.05% trypsin/EDTA solution for two minutes). Cells were then pelleted, resuspended in a small volume, and counted. About 5000 cells were plated in a 35 mm dish (Corning or Nunc).

NEP cells derived from E10.5 embryos were expanded in the presence of FGF and CEE for 5 days and differentiated by replating on laminin in the presence of CEE. Differentiating NEP cells were triple-labeled with antibodies to B-NCAM, GFAP, and GalC. This showed that E-NCAM-immunoreactive cells that differentiated from NEP cells did not express astrocytic (GFAP) or oligodendrocytic (GalC) markers, A sister plate was double-labeled with antibodies to E-NCAM and nestin. This showed that E-NCAM immunoreactive cells that differentiated from NEP cells co-express nestin. Differentiating NEP cells were incubated for 24 hours with BrdU and subsequently double-labeled with an antibody against BrdU and E-NCAM. This showed that most E-NCAM-immunoreactive cells divided in 24 hours. This higher labeling rate may reflect differences in the isolate procedure as compared to the previous example. Table 5 summarizes the antigenic profile of E-NCAM$^+$ cells derived from E10.5 NEP cells. Note that NEP-derived E-NCAM$^+$ cells are antigenically similar to E13.5 E-NCAM$^+$ cells and, like E13.5 E-NCAM$^+$, do not express any of the glial markers examined.

TABLE 5

| Antigen | Expression |
| --- | --- |
| α-Nestin | +/− |
| α-β-III tubulin* | + |
| A2B5 | − |
| α-GFAP | − |
| α-GalC | − |

*A subset of cells express this marker.

Thus, induced NEP cultures comprise multiple phenotypes, including E-NCAM$^+$ cells. Like the E13.5 E-NCAM$^+$ cells, NEP-derived E-NCAM$^+$ cells did not express glial markers, but co-expressed β-III tubulin (20–30%) and nestin (70–80%) immunoreactivity. Ninety percent of panned E-NCAM$^+$ cells incorporated BrdU in culture and generated neurons after addition of RA or NT-3 and thus appeared similar to the E13.5 E-NCAM-immunoreactive cells.

EXAMPLE 9

To determine whether single NEP-derived E-NCAM$^+$ cells were also restricted to neurons in their differentiation potential, cells were studied in clonal culture. NEP cells were induced to differentiate by replating on laminin and withdrawal of CEE, as described in Ser. No. 08/852,744, now U.S. Pat. No. 6,361,996, NEP cells derived from E10.5 embryos were expanded in the presence of FGF and CEE for 5 days and differentiated by replating on laminin in the absence of CEE. Immunopanned E-NCAM-immunoreactive cells were then plated on clonal-grid dishes (Greiner Labortechnik) coated with fibronectin/laminin, and single cells were followed in culture. After 5 days, clones were switched to RA and FGF was withdrawn. Clones were allowed to grow for an additional 3 days, fixed with paraformaldehyde, and triple-labeled with A2B5 and antibodies against GFAP and β-III tubulin. In addition, cells were counterstained with DAPI to show individual cell nuclei. Table 6 summarizes the results of the staining of all 47 clones studied (8 of 47 clones did not survive replating). Note that no clone contained astrocytes (GFAP$^+$) cells or glial precursor cells (A2B5$^+$).

TABLE 6

| Antigen Expressed | % of Clones |
|---|---|
| α-β-III tubulin | 100% |
| A2B5 | 0% |
| α-GFAP | 0% |

Forty-eight hours after cells were induced to differentiate, 10–30% of the cells had begun to express E-NCAM immunoreactivity. NEP-cell-derived E-NCAM$^+$ cells were selected by immunopanning according to the procedure of Example 3, and individual E-NCAM$^+$ cells were plated in medium containing FGF and NT-3 and clones were analyzed after 10 days.

All clones contained only E-NCAM$^+$/β-III-tubulin$^+$ cells, but not GFAP or A2B5 immunoreactive cells. In addition, individual E-NCAM$^+$ cells failed to differentiate into oligodendrocytes or astrocytes under culture conditions that promoted astrocytic and oligodendroglial differentiation from the parent NEP cell population. E-NCAM$^+$ cells could be maintained as dividing precursor cells in defined medium in the presence of high concentrations of FGF (10 ng/ml) and NT-3 (10 ng/ml). E-NCAM$^+$ cells maintained for up to three months could readily differentiate into β-III tubulin+mature neurons that expressed a variety of neurotransmitter phenotypes when exposed to RA grown on laminin. Thus, E-NCAM$^+$ cells are similar to E13.5 neuronal precursors in their differentiation potential, antigenic profile, and in the conditions optimal for extended growth as a dividing precursor cell population.

EXAMPLE 10

Differentiation of the E-NCAM$^+$ population from an apparently homogeneous Nestin$^+$/E-NCAM$^-$ NEP cell population suggests a progressive restriction in developmental fate. It was thought possible, but unlikely, that individual NEP cells could be pre-committed to generating neuroblasts or glioblasts. To rule out this possibility, individual NEP clones were examined for their ability to generate E-NCAM-immunoreactive cells and A2B5-immunoreactive cells. A2B5 and E-NCAM were chosen since it had previously been shown that A2B5 immunoreactivity is unique to oligodendrocyte-astrocyte precursors at this stage of development. NEP cells derived from E10.5 embryos were expanded in the presence of FGF and CEE for 5 days, harvested by trypsinization, and replated at clonal density in gridded clonal dishes. After 7 days in culture, individual clones were double-labeled with antibodies against E-NCAM and A2B5 according to the procedure of Example 2. Of 112 NEP clones that were followed in culture, 83% generated both A2B5 and E-NCAM immunoreactive cells. Five percent of the clones consisted of only A2B5 immunoreactive cells, and 12% of the clones showed no convincing staining for either A2B5 or E-NCAM immunoreactivity. In all clones tested, E-NCAM and A2B5 were expressed in non-overlapping populations. That is, no cell co-expressed both markers. Table 7 summarizes the results obtained with 112 clones.

TABLE 7

| Antigen Expressed | % of Clones | Number of Clones |
|---|---|---|
| E-NCAM$^+$/A2B5$^+$ | 83% | 93 |
| A2B5$^+$ alone | 5% | 6 |
| E-NCAM$^-$/A2B5$^-$ | 12% | 13 |

Thus, the majority of NEP cells appear to be capable of generating precursors for glial restricted cells as well as neuronal restricted precursors.

EXAMPLE 11

To test if most neurons were generated via an E-NCAM$^+$ intermediate neuroblast, complement-mediated cell lysis was utilized to selectively kill E-NCAM$^+$ cells. Twenty-four hours after replating NEP cells in differentiating conditions, E-NCAM-immunoreactive cells were killed using an IgM antibody to E-NCAM and guinea pig complement. In sister plates, glial precursors were killed using an anti-A2B5 IgM antibody and complement. At this stage in development, most E-NCAM$^+$ cells do not express β-III tubulin. Treated plates were allowed to differentiate for an additional three days, and the development of neurons was monitored. E-NCAM-mediated lysis significantly reduced the number of β-III tubulin-immunoreactive cells that developed when compared to cultures treated with A2B5 (219±35 versus 879±63, respectively) suggesting that neuronal differentiation from NEP cells in vitro requires a transition through an E-NCAM immunoreactive state.

We claim:

1. A population of mitotic, self-renewing lineage-restricted neuronal precursor cells wherein greater than 95% of said population is E-NCAM positive, said cells being isolated by immunoselection using an antibody against polysialated N-CAM from a sample of central nervous system tissue from a mammalian embryo at a stage of embryonic development after closure of the neural tube but prior to differentiation of glial and neuronal cells in the neural tube, wherein said cells require FGF for self-renewal and proliferation, grow over multiple passages in mass and clonal culture, and differentiate into neurons, but not into astrocytes and oligodendrocytes.

* * * * *